United States Patent [19]

Farber

[11] Patent Number: 5,236,829
[45] Date of Patent: Aug. 17, 1993

[54] METHOD OF PRODUCING MONOKINE INDUCED BY GAMMA INTERFERON

[75] Inventor: Joshua Farber, Baltimore, Md.

[73] Assignee: The Johns Hopkins University, Baltimore, Md.

[21] Appl. No.: 624,742

[22] Filed: Dec. 10, 1990

[51] Int. Cl.$^5$ .................... C07H 15/12; C07H 17/00; C12P 21/06; C12N 5/00
[52] U.S. Cl. .................... 435/69.1; 435/240.2; 435/320.1; 536/23.5; 536/23.51; 530/350; 530/351; 530/387.9; 530/389.2
[58] Field of Search .................... 435/69.1, 240.2, 320.1, 435/240.1; 536/27; 530/350, 387, 351; 424/85.8

[56] References Cited

PUBLICATIONS

Vanguri et al., (1990), JBC, vol. 265, No. 25, pp. 15049-15057.
Stoeckle and Barker, "Two Burgeoning Families of Platelet Factor 4-Related Proteins: Mediators of the Inflammatory Response", The New Biologist, vol. 2, No. 4 (Apr.), 1990; pp. 313-323.
Farber, Second International Workshop on Cytokines, 1989, Abstract.
Farber, "A Macrophage mRNA Selectively Induced by alpha-interferon Encodes a Member of the Platelet Factor 4 Family of Cytokines", Proc. Natl. Acad. Sci., USA, vol. 87, pp. 5238-5242, Jul. 1990.

Primary Examiner—Robert J. Hill, Jr.
Assistant Examiner—Gian P. Wang
Attorney, Agent, or Firm—Banner, Birch, McKie & Beckett

[57] ABSTRACT

Monokines are provided which are produced by monocytic cells of mammals which have been stimulated with interferon-γ. cDNA sequences encoding the monokines are also disclosed. Methods of producing the mammalian monokines are taught. The monokines are implicated in immunological and inflammatory processes, as are other members of the platelet factor 4 family of cytokines.

12 Claims, 12 Drawing Sheets

```
                    TTTCCTAAATAAATATGATCCCCAAGAACATGCTCTCTAAAGACATTCTCG      14
                                                       ↑
        GACTTCACTCCAACACAGTGACTC
                CACTCCAACACAGTGACTCAATAGAACTCAGCTCTGCC ATG AAG TCC GCT GTT      72
        1                                              MET Lys Ser Ala Val

CTT TTC CTT TTG GGC ATC ATC TTC CTG GAG CAG TGT GGA GTT CGA GGA|     120
     6  Leu Phe Leu Leu Gly Ile Ile Phe Leu Glu Gln Cys Gly Val Arg Gly

ACC CTA GTG ATA AGG AAT GCA CGA TGC TCC TGC ATC AGC ACC AGC CGA      168
     22 Thr Leu Val Ile Arg Asn Ala Arg Cys Ser Cys Ile Ser Thr Ser Arg

GGC ACG ATC CAC TAC AAA TCC CTC AAA GAC CTC AAA CAG TTT GCC CCA      216
     38 Gly Thr Ile His Tyr Lys Ser Leu Lys Asp Leu Lys Gln Phe Ala Pro

AGC CCC AAT TGC AAC AAA ACT GAA ATC ATT GCT ACA CTG AAG AAC GGA      264
     54 Ser Pro Asn Cys Asn Lys Thr Glu Ile Ile Ala Thr Leu Lys Asn Gly

GAT CAA ACC TGC CTA GAT CCG GAC TCG GCA AAT GTG AAG AAG CTG ATG      312
     70 Asp Gln Thr Cys Leu Asp Pro Asp Ser Ala Asn Val Lys Lys Leu Met

AAA GAA TGG GAA AAG AAG ATC AAC CAA AAG AAA AAG CAA AAG AGG GGG      360
     86 Lys Glu Trp Glu Lys Lys Ile Asn Gln Lys Lys Lys Gln Lys Arg Gly

AAA AAA CAT CAA AAG AAC ATG AAA AAC AGA AAA CCC AAA ACA CCC CAA      408
     102 Lys Lys His Gln Lys Asn Met Lys Asn Arg Lys Pro Lys Thr Pro Gln

AGT CGT CGT CGT TCA AGG AAG ACT ACA TAA GAGACCATTACTTTACCAACAAG      461
     118 Ser Arg Arg Arg Ser Arg Lys Thr Thr *

CACCCTGAATCTTAATGGGTTTTAGATTGTACTGAAAAGCCTTCCCTGGCAGAGCAGCCTTTA      524
        ATACATAGGCTTTTAATACATTAACTCAACTACAAAACATAAAGTGTTAATTTGAAATTATAA      587
        CTAACTTTAGGAAGTTAATTGCAAAACTCCAATAGTAACAATTGCTAGAGGCAAAAACTCTGT      650
        GTTCTACACAGCCAACAAAATTTCATCACGCCCTTGAGCCTAGTCGTGATAACATCAGATCTG      713
        GGCAAGTGTCCCTTTCCTTCATAGCTATCCAATGCACAACAGCTGTCTGGCTTCCAGAGCCAC      776
        ACATTTGGCAGCCTCCGGAGACTTCTGAGGCTCACCAAGTCCCAGGCCTGTCTGTTTG        839
        CTGGTGAGCTAGATAGACCTCACCAAGCTGGAGAGGCCCTCGGCAGCTGCATTTGGGTCAGCC      902
        TAGAGCCCCTGCACACATTGTGTCTCAGAGATGGTGCTAATGGTTTTGGGGTTCTACAGTGGA      965
        GACCACCAGAGTTGGCCTTCAGAACCTCCCACGTAGCTTTCGAGACCATGGGATTTCATTATT     1028
        AACTTGATCCCATCTTCAGAGCTTATTCTAAGTTTGCCTCTTCAATAAAACTCTCCTAGAAGG     1091
        TTGTGGCTGTAGCTTAGTGGCAGAACACTTGGTGTTGCAGGGACCAGGTCCTTCACTAACAGT     1154
        GCAAAAACTTAACCAATTTAAAGAACATTTTCTGGCTACTCAAATTCTCTTAAATTTATTCCT     1217
        GTTTCACAAGTAAACACTTCGCTGCTATCTAc                                    1248
```

FIG. 3

```
                  TTTCCTAAATAAATATGATCCCCAAGAACATGCTCTCTAAAGACATTCTCG       14
                                                       ↑
     GACTTCACTCCAACACAGTGACTC
              CACTCCAACACAGTGACTCAATAGAACTCAGCTCTGCC ATG AAG TCC GCT GTT    72
   1                                                 MET Lys Ser Ala Val

CTT TTC CTT TTG GGC ATC ATC TTC CTG GAG CAG TGT GGA GTT CGA GGA        120
   6 Leu Phe Leu Leu Gly Ile Ile Phe Leu Glu Gln Cys Gly Val Arg Gly

ACC CTA GTG ATA AGG AAT GCA CGA TGC TCC TGC ATC AGC ACC AGC CGA        168
  22 Thr Leu Val Ile Arg Asn Ala Arg Cys Ser Cys Ile Ser Thr Ser Arg

GGC ACG ATC CAC TAC AAA TCC CTC AAA GAC CTC AAA CAG TTT GCC CCA        216
  38 Gly Thr Ile His Tyr Lys Ser Leu Lys Asp Leu Lys Gln Phe Ala Pro

AGC CCC AAT TGC AAC AAA ACT GAA ATC ATT GCT ACA CTG AAG AAC GGA        264
  54 Ser Pro Asn Cys Asn Lys Thr Glu Ile Ile Ala Thr Leu Lys Asn Gly

GAT CAA ACC TGC CTA GAT CCG GAC TCG GCA AAT GTG AAG AAG CTG ATG        312
  70 Asp Gln Thr Cys Leu Asp Pro Asp Ser Ala Asn Val Lys Lys Leu Met

AAA GAA TGG GAA AAG AAG ATC AAC CAA AAG AAA AAG CAA AAG AGG GGG        360
  86 Lys Glu Trp Glu Lys Lys Ile Asn Gln Lys Lys Lys Gln Lys Arg Gly

AAA AAA CAT CAA AAG AAC ATG AAA AAC AGA AAA CCC AAA ACA CCC CAA        408
 102 Lys Lys His Gln Lys Asn Met Lys Asn Arg Lys Pro Lys Thr Pro Gln

AGT CGT CGT CGT TCA AGG AAG ACT ACA TAA GAGACCATTACTTTACCAACAAG        461
 118 Ser Arg Arg Arg Ser Arg Lys Thr Thr  *

CACCCTGAATCTTAATGGGTTTTAGATTGTACTGAAAAGCCTTCCCTGGCAGAGCAGCCTTTA       524
     ATACATAGGCTTTTAATACATTAACTCAACTACAAAACATAAAGTGTTAATTTGAAATTATAA       587
     CTAACTTTAGGAAGTTAATTGCAAAACTCCAATAGTAACAATTGCTAGAGGCAAAAACTCTGT       650
     GTTCTACACAGCCAACAAAATTTCATCACGCCCTTGAGCCTAGTCGTGATAACATCAGATCTG       713
     GGCAAGTGTCCCTTTCCTTCATAGCTATCCAATGCACAACAGCTGTCTGGCTTCCAGAGCCAC       776
     ACATTTGGCAGCCTCCGGAGACTTCTGAGGCTCACGTCACCAAGTCCCAGGCCTGTCTGTTTG       839
     CTGGTGAGCTAGATAGACCTCACCAAGCTGGAGAGGCCCTCGGCAGCTGCATTTGGGTCAGCC       902
     TAGAGCCCCTGCACACATTGTGTCTCAGAGATGGTGCTAATGGTTTTGGGGTTCTACAGTGGA       965
     GACCACCAGAGTTGGCCTTCAGAACCTCCCACGTAGCTTTCGAGACCATGGGATTTCATTATT      1028
     AACTTGATCCCATCTTCAGAGCTTATTCTAAGTTTGCCTCTTCAATAAAACTCTCCTAGAAGG      1091
     TTGTGGCTGTAGCTTAGTGGCAGAACACTTGGTGTTGCAGGGACCAGGTCCTTCACTAACAGT      1154
     GCAAAAACTTAACCAATTTAAAGAACATTTTCTGGCTACTCAAATTCTCTTAAATTTATTCCT      1217
     GTTTCACAAGTAAACACTTCGCTGCTATCTA.                                     1248
```

FIG. 4

```
MKS....FW..G...EOC.VR.T.L..N........
MNOSAAVIFCLLLEGLS.TO.IPLA.TV.L........
MNOTALLICCLL.TLSS.IO.VPLS.RTV.........
MIPATRSL..CAALLLLATSRLATG.API.NEL-
-PSNPRLLR.AL.LL.VAAGRAA.AS.ATEL.-
MTSKLAV.L.AAFL.SAALCE.AVLPRSAKEL-
      NLAKGKEESLDSDLYAEL.-
      EAE.EDGDLQ.-
MNGKLG....A.L.LVSAALSQ.RTLVKMGNEL.-
```

```
S ......RT..Y......OFA.N      m119
N ...HIDD.PVRMRAIGK.EIIPA.LS  mCRG-2
T ...N.PVNPR..EK.EIIPA.OF     hIP-10
Q ...LN.OS..VLPSG.H           mKC/Gro
Q ..LQ.L...P..NIOSVNVKS.H     hGro/MGSA
O ..VK.YSKPF.F.I.E.RVIESG.H   hNAP/IL-8
M ..VK.TS...P.NIOS.EVIGKGTH   hCTAP III
L .-TSOVRPRHITS.EVIKAGH       hPF 4
Q .HSKF..P.IO.V.LTPSG.H       c9E3
```

```
  ....DT.......ANT......EWE.-
  ....DE.R......NE.KTIN..AFSO.M-
  ....E.R......NE.KAILN..LAVS.E-
  ......EA....PEAPLO..IVOKHL.G-
  ......KA....NAPI..IEKMLNS-
  ..V.S....EL..O.V.VEKFL.R-
  ..V.V.S..REL..KENW.ORVVEKFL.R-
  ..G.K..I....ORV.KI.LVOKKLAG-
  ..G.K.I....OAPRI.IVOKKLAG-
  .......I....OLOAPLYK...KLLES-
  .G..REV..L.YMT.APW.OLIVEALMAK-
```

HOMOLOGY TO m119

|  | TOTAL Values (%) | CYS WINDOW Values (%) |
|---|---|---|
| mCRG-2 | 31/96(32) | 16/45(36) |
| hIP-10 | 32/96(33) | 18/45(40) |
| mKC/Gro | 31/94(33) | 22/44(50) |
| hGro/MGSA | 33/95(35) | 21/44(48) |
| hNAP/IL-8 | 27/95(28) | 17/44(39) |
| hCTAP III | 24/86(28) | 18/44(41) |
| hPF4 | 18/71(25) | 13/44(30) |
| mMIP-2 | 4/32(13) | 3/22(14) |
| c9E3 | 34/103(33) | 22/44(50) |

FIG. 5

```
              10                  30                  50
     atccaatacaggagtgacttggaactccattctatcactatgaagaaaagtggtgttctt
 1   ----------+---------+---------+---------+---------+---------+  60
     taggttatgtcctcactgaaccttgaggtaagatagtgatacttcttttcaccacaagaa
                                              MetLysLysSerGlyValLeu
                                                M  K  K  S  G  V  L

              70                  90                 110
     ttcctcttgggcatcatcttgctggttctgattggagtgcaaggaacccccagtagtgaga
61   ----------+---------+---------+---------+---------+---------+ 120
     aaggagaacccgtagtagaacgaccaagactaacctcacgttccttgggg tcatcactct
     PheLeuLeuGlyIleIleLeuLeuValLeuIleGlyValGlnGlyThrProValValArg
      F  L  L  G  I  I  L  L  V  L  I  G  V  Q  G  T  P  V  V  R

             130                 150                 170
     aagggtcgctgttcctgcatcagcaccaaccaagggactatccacctacaatccttgaaa
121  ----------+---------+---------+---------+---------+---------+ 180
     ttcccagcgacaaggacgtagtcgtggttggttccctgataggtggatgttaggaacttt
     LysGlyArgCysSerCysIleSerThrAsnGlnGlyThrIleHisLeuGlnSerLeuLys
      K  G  R  C  S  C  I  S  T  N  Q  G  T  I  H  L  Q  S  L  K

             190                 210                 230
     gaccttaaacaatttgccccaagcccttcctgcgagaaaattgaaatcattgctacactg
181  ----------+---------+---------+---------+---------+---------+ 240
     ctggaatttgttaaacggggttcgggaaggacgctcttttaactttagtaacgatgtgac
     AspLeuLysGlnPheAlaProSerProSerCysGluLysIleGluIleIleAlaThrLeu
      D  L  K  Q  F  A  P  S  P  S  C  E  K  I  E  I  I  A  T  L

             250                 270                 290
     aagaatggagttcaaacatgtctaaacccagattcagcagatgtgaaggaactgattaaa
241  ----------+---------+---------+---------+---------+---------+ 300
     ttcttacctcaagtttgtacagatttgggtctaagtcgtctacacttccttgactaattt
     LysAsnGlyValGlnThrCysLeuAsnProAspSerAlaAspValLysGluLeuIleLys
      K  N  G  V  Q  T  C  L  N  P  D  S  A  D  V  K  E  L  I  K

             310                 330
     aagtgggagaaacaggtcagccaaaagaaaaagc...
301  ----------+---------+---------+---- 334
     ttcaccctctttgtccagtcggttttcttttcg...
     LysTrpGluLysGlnValSerGlnLysLysLys...
      K  W  E  K  Q  V  S  Q  K  K  K

```

FIG. 6

Comparison: MIG-2 and MIG

```
MIG-2    MKKSGVLFPLLGIILLVLIGVQGTPVVRKGRCSCISTNQGTIHLQSLKDLKQFAPSPS
         ||  ||||||||||  ||  ||  |||||||||||  ||||||||||||||||||||
119/MIG  MK-SaVLFLLGIIiLegcGVrGTlViRnaRCSCISTsrGTIHykSLKDLKQFAPSPn MIG-2    CEKIEIIATLKNGVQTCLNPDSADVKELIKKWEKQVSQKKKQKNGKKHQKK-KVLKV
          | ||||||||||| ||| |||| | |||| |||| |  ||||| |||||| ||||
119/MIG  CnKtEIIATLKNGdQTCLdPDSAnVKklmKeWEKkinQKKKQKrGKKHQKnmKnrKp MIG-2    RKSQ-RSRQKKTT    125
         |  | | | ||||
119/MIG  ktpQsRrRsrKTT    126
```

INDUCTION OF MIG2 mRNA IN
HUMAN MONOCYTIC CELLS BY IFN-γ

SEQUENCE LISTING ( 1 ) GENERAL INFORMATION:

( i i i ) NUMBER OF SEQUENCES: 4

( 2 ) INFORMATION FOR SEQ ID NO:1:

( i ) SEQUENCE CHARACTERISTICS:
        ( A ) LENGTH: 126 amino acids
        ( B ) TYPE: amino acid
        ( D ) TOPOLOGY: linear ( i i ) MOLECULE TYPE: protein ( x i ) SEQUENCE DESCRIPTION: SEQ ID NO:1:

```
Met Lys Ser Ala Val Leu Phe Leu Leu Gly Ile Ile Phe Leu Glu Gln
 1           5                   10                  15
Cys Gly Val Arg Gly Thr Leu Val Ile Arg Asn Ala Arg Cys Ser Cys
             20                  25                  30
Ile Ser Thr Ser Arg Gly Thr Ile His Tyr Lys Ser Leu Lys Asp Leu
         35                  40                  45
Lys Gln Phe Ala Pro Ser Pro Asn Cys Asn Lys Thr Glu Ile Ile Ala
     50                  55                  60
Thr Leu Lys Asn Gly Asp Gln Thr Cys Leu Asp Pro Asp Ser Ala Asn
 65                  70                  75                  80
Val Lys Lys Leu Met Lys Glu Trp Glu Lys Lys Ile Asn Gln Lys Lys
                 85                  90                  95
Lys Gln Lys Arg Gly Lys Lys His Gln Lys Asn Met Lys Asn Arg Lys
             100                 105                 110
Pro Lys Thr Pro Gln Ser Arg Arg Arg Ser Arg Lys Thr Thr
         115                 120                 125
```

( 2 ) INFORMATION FOR SEQ ID NO:2:

( i ) SEQUENCE CHARACTERISTICS:
        ( A ) LENGTH: 1285 base pairs
        ( B ) TYPE: nucleic acid
        ( C ) STRANDEDNESS: double
        ( D ) TOPOLOGY: linear ( i i ) MOLECULE TYPE: cDNA ( i i i ) HYPOTHETICAL: NO ( i v ) ANTI-SENSE: NO ( v i ) ORIGINAL SOURCE:
        ( A ) ORGANISM: Mus spp.
        ( H ) CELL LINE: RAW 264.7

( i x ) FEATURE:
        ( A ) NAME/KEY: CDS
        ( B ) LOCATION: 95..475

( x i ) SEQUENCE DESCRIPTION: SEQ ID NO:2:

```
TTTCCTAAAT AAATATGATC CCCAAGAACA TGCTCTCTAA AGACATTCTC GGACTTCACT            60

CCAACACAGT GACTCAATAG AACTCAGCTC TGCC ATG AAG TCC GCT GTT CTT            112
                                      Met Lys Ser Ala Val Leu
                                       1               5

TTC CTT TTG GGC ATC ATC TTC CTG GAG CAG TGT GGA GTT CGA GGA ACC            160
Phe Leu Leu Gly Ile Ile Phe Leu Glu Gln Cys Gly Val Arg Gly Thr
         10                  15                  20

CTA GTG ATA AGG AAT GCA CGA TGC TCC TGC ATC AGC ACC AGC CGA GGC            208
```

```
Leu Val Ile Arg Asn Ala Arg Cys Ser Cys Ile Ser Thr Ser Arg Gly
        25                  30                  35

ACG ATC CAC TAC AAA TCC CTC AAA GAC CTC AAA CAG TTT GCC CCA AGC        256
Thr Ile His Tyr Lys Ser Leu Lys Asp Leu Lys Gln Phe Ala Pro Ser
    40                  45                  50

CCC AAT TGC AAC AAA ACT GAA ATC ATT GCT ACA CTG AAG AAC GGA GAT        304
Pro Asn Cys Asn Lys Thr Glu Ile Ile Ala Thr Leu Lys Asn Gly Asp
 55                  60                  65                  70

CAA ACC TGC CTA GAT CCG GAC TCG GCA AAT GTG AAG AAG CTG ATG AAA        352
Gln Thr Cys Leu Asp Pro Asp Ser Ala Asn Val Lys Lys Leu Met Lys
                75                  80                  85

GAA TGG GAA AAG AAG ATC AAC CAA AAG AAA AAG CAA AAG AGG GGG AAA        400
Glu Trp Glu Lys Lys Ile Asn Gln Lys Lys Lys Gln Lys Arg Gly Lys
                90                  95                  100

AAA CAT CAA AAG AAC ATG AAA AAC AGA AAA CCC AAA ACA CCC CAA AGT        448
Lys His Gln Lys Asn Met Lys Asn Arg Lys Pro Lys Thr Pro Gln Ser
        105                 110                 115

CGT CGT CGT TCA AGG AAG ACT ACA TAAGAGACCA TTACTTTACC AACAAGCACC       502
Arg Arg Arg Ser Arg Lys Thr Thr
        120                 125

CTGAATCTTA ATGGGTTTTA GATTGTACTG AAAAGCCTTC CCTGGCAGAG CAGCCTTTAA      562

TACATAGGCT TTTAATACAT TAACTCAACT ACAAAACATA AAGTGTTAAT TTGAAATTAT      622

AACTAACTTT AGGAAGTTAA TTGCAAAACT CCAATAGTAA CAATTGCTAG AGGCAAAAAC      682

TCTGTGTTCT ACACAGCCAA CAAAATTTCA TCACGCCCTT GAGCCTAGTC GTGATAACAT      742

CAGATCTGGG CAAGTGTCCC TTTCCTTCAT AGCTATCCAA TGCACAACAG CTGTCTGGCT      802

TCCAGAGCCA CACATTTGGC AGCCTCCGGA GACTTCTGAG GCTCACGTCA CCAAGTCCCA      862

GGCCTGTCTG TTTGCTGGTG AGCTAGATAG ACCTCACCAA GCTGGAGAGG CCCTCGGCAG      922

CTGCATTTGG GTCAGCCTAG AGCCCCTGCA CACATTGTGT CTCAGAGATG GTGCTAATGG      982

TTTTGGGGTT CTACAGTGGA GACCACCAGA GTTGGCCTTC AGAACCTCCC ACGTAGCTTT     1042

CGAGACCATG GGATTTCATT ATTAACTTGA TCCCATCTTC AGAGCTTATT CTAAGTTTGC     1102

CTCTTCAATA AAACTCTCCT AGAAGGTTGT GGCTGTAGCT TAGTGGCAGA ACACTTGGTG     1162

TTGCAGGGAC CAGGTCCTTC ACTAACAGTG CAAAAACTTA ACCAATTTAA AGAACATTTT     1222

CTGGCTACTC AAATTCTCTT AAATTTATTC CTGTTTCACA AGTAAACACT TCGCTGCTAT     1282

CTA                                                                  1285
```

( 2 ) INFORMATION FOR SEQ ID NO:3:

( i ) SEQUENCE CHARACTERISTICS:
        ( A ) LENGTH: 125 amino acids
        ( B ) TYPE: amino acid
        ( D ) TOPOLOGY: linear ( i i ) MOLECULE TYPE: protein ( x i ) SEQUENCE DESCRIPTION: SEQ ID NO:3:

```
Met Lys Lys Ser Gly Val Leu Phe Leu Leu Gly Ile Ile Leu Leu Val
 1               5                   10                  15

Leu Ile Gly Val Gln Gly Thr Pro Val Val Arg Lys Gly Arg Cys Ser
            20                  25                  30

Cys Ile Ser Thr Asn Gln Gly Thr Ile His Leu Gln Ser Leu Lys Asp
            35                  40                  45

Leu Lys Gln Phe Ala Pro Ser Pro Ser Cys Glu Lys Ile Glu Ile Ile
         50                  55                  60

Ala Thr Leu Lys Asn Gly Val Gln Thr Cys Leu Asn Pro Asp Ser Ala
 65                  70                  75                  80
```

-continued

```
Asp Val Lys Glu Leu Ile Lys Lys Trp Glu Lys Gln Val Ser Gln Lys
             85                  90                  95

Lys Lys Gln Lys Asn Gly Lys Lys His Gln Lys Lys Lys Val Leu Lys
            100                 105                 110

Val Arg Lys Ser Gln Arg Ser Arg Gln Lys Lys Thr Thr
            115                 120                 125
```

( 2 ) INFORMATION FOR SEQ ID NO:4:

( i ) SEQUENCE CHARACTERISTICS:
        ( A ) LENGTH: 417 base pairs
        ( B ) TYPE: nucleic acid
        ( C ) STRANDEDNESS: double
        ( D ) TOPOLOGY: linear ( i i ) MOLECULE TYPE: cDNA ( i i i ) HYPOTHETICAL: NO ( i v ) ANTI-SENSE: NO ( v i ) ORIGINAL SOURCE:
        ( A ) ORGANISM: Homo sapiens ( i x ) FEATURE:
        ( A ) NAME/KEY: CDS
        ( B ) LOCATION: 40..414

( x i ) SEQUENCE DESCRIPTION: SEQ ID NO:4:

```
ATCCAATACA GGAGTGACTT GGAACTCCAT TCTATCACT ATG AAG AAA AGT GGT         54
                                           Met Lys Lys Ser Gly
                                            1               5

GTT CTT TTC CTC TTG GGC ATC ATC TTG CTG GTT CTG ATT GGA GTG CAA       102
Val Leu Phe Leu Leu Gly Ile Ile Leu Leu Val Leu Ile Gly Val Gln
             10                  15                  20

GGA ACC CCA GTA GTG AGA AAG GGT CGC TGT TCC TGC ATC AGC ACC AAC       150
Gly Thr Pro Val Val Arg Lys Gly Arg Cys Ser Cys Ile Ser Thr Asn
             25                  30                  35

CAA GGG ACT ATC CAC CTA CAA TCC TTG AAA GAC CTT AAA CAA TTT GCC       198
Gln Gly Thr Ile His Leu Gln Ser Leu Lys Asp Leu Lys Gln Phe Ala
             40                  45                  50

CCA AGC CCT TCC TGC GAG AAA ATT GAA ATC ATT GCT ACA CTG AAG AAT       246
Pro Ser Pro Ser Cys Glu Lys Ile Glu Ile Ile Ala Thr Leu Lys Asn
     55                  60                  65

GGA GTT CAA ACA TGT CTA AAC CCA GAT TCA GCA GAT GTG AAG GAA CTG       294
Gly Val Gln Thr Cys Leu Asn Pro Asp Ser Ala Asp Val Lys Glu Leu
 70                  75                  80                  85

ATT AAA AAG TGG GAG AAA CAG GTC AGC CAA AAG AAA AAG CAA AAG AAT       342
Ile Lys Lys Trp Glu Lys Gln Val Ser Gln Lys Lys Lys Gln Lys Asn
                 90                  95                 100

GGG AAA AAA CAT CAA AAA AAG AAA GTT CTG AAA GTT CGA AAA TCT CAA       390
Gly Lys Lys His Gln Lys Lys Lys Val Leu Lys Val Arg Lys Ser Gln
            105                 110                 115

CGT TCT CGT CAA AAG AAG ACT ACA TAA                                   417
Arg Ser Arg Gln Lys Lys Thr Thr
            120             125
```

METHOD OF PRODUCING MONOKINE INDUCED BY GAMMA INTERFERON

The invention described herein was made with government support under a grant from the Department of Health and Human Services. The U.S. Government retains certain rights in this invention.

TECHNICAL FIELD OF THE INVENTION

This invention relates to the area of cytokines. More particularly it relates to cytokines that are members of the platelet factor 4 family.

BACKGROUND OF THE INVENTION

Activated macrophages exhibit a wide range of activities, including the presentation of antigen, the recruitment of inflammatory cells, the stimulation of cell growth, and the destruction of pathogens and tumor cells. Cytokines play a central role in macrophage physiology, both as macrophage activators (Adams, (1989) Immunol. Today 10:33–35) and as mediators of macrophage activities (Nathan, (1987) J. Clin. Invest. 79:319–326). The best characterized macrophage-activating cytokine is γ-interferon (IFN-γ), which is able to induce the expression of major histocompatibility complex class II antigens (Rosa, et al. (1983) EMBO J. 2:1585–1589), prime macrophages for the release of reactive oxygen intermediates that are important for pathogen and tumor cell killing (Nathan, et al. (1984) J. Exp. Med. 160:600–605), and enhance the expression of the pleiotropic macrophage products tumor necrosis factor (TNF) and interleukin 1 (IL-1) (Collart, et al. (1986), J. Exp. Med. 164:2113–2118.

IFN-γ(type II IFN) and other macrophage activators such as lipopolysaccharide (LPS) and type I IFN (IFN-α and IFN-β) act by altering gene expression (Revel, et al. (1986) Trends Biochem. Sci. 11:166–170; Tannenbaum, et al. (1988), J. Immunol. 140:3640–3645)). While the sets of genes induced by these factors overlap, genes have been identified that are activated preferentially by type II IFN (Luster, et al., (1985) Nature 315:672–676; Fan, et al., (1989) Mol. Cell. Biol. 9:1922–1928) or by type I IFN (Revel, et al. supra) or by LPS (Tannebaum, et al., supra). As regards the IFNs, the molecular mechanisms whereby genes are differentially regulated by type I and type II IFNs are unknown.

The cytokines produced by activated macrophages include, in addition to extensively studied mediators such as TNF and IL-1, secreted proteins such as the members of the platelet factor 4 (PF4) family, including IP-10 (Luster, et al., (1985) Nature 315:672–676), IL-8 (Matsushima, et al. (1988), J. Exp. Med. 167:1883–1893), and macrophage inflammatory protein 2 (MIP-2) (Wolpe, et al., (1989) Proc. Natl. Acad. Sci., USA 86:612–1893). Both IL-8 and MIP-2 have been shown to be chemoattractants for human neutrophils, and IL-8 has been found to modulate neutrophil adherence to endothelial cells (Gimbrone, et al. (1989) Science 246:1601–1603).

It is presumed that there are as yet undiscovered macrophage products that function as mediators for some of the activities of activated macrophages. There is a need in the art to know how activated macrophages exert their effects and to identify and isolate the factors which mediate macrophage activities.

SUMMARY OF THE INVENTION

It is an object of the invention to provide a new mammalian cytokine.

It is another object of the invention to provide a DNA molecule which encodes a new mammalian cytokine.

It is yet another object of the invention to provide a host cell which contains a cDNA molecule encoding a new mammalian cytokine.

It is still another object of the invention to provide a method of producing a new mammalian cytokine.

It is an object of the invention to provide nucleotide probes which hydridize to DNA molecules encoding the new mammalian cytokine.

It is still another object to provide antibodies which are specifically immunoreactive with a new mammalian cytokine.

It is yet another object of the invention to provide receptors which specifically bind to a new mammalian cytokine, via which the cytokine exerts its effects on susceptible cells.

These and other objects of the invention are provided by one or more of the embodiments which are described below. In one embodiment of the invention an intron-free DNA molecule encoding a mammalian MIG is provided which hybridizes to a second DNA molecule having a nucleotide sequence as shown in SEQ ID NO: 2 or 4.

In another embodiment of the invention an interferon-gamma-inducible mammalian protein is provided which is encoded by an intron-free DNA molecule which hybridizes to a second DNA molecule having a nucleotide sequence as shown in SEQ ID NO: 2 or 4, and which is substantially free of other mammalian proteins.

In still another embodiment of the invention a host cell is provided that contains an intron-free DNA molecule encoding a mammalian MIG which hybridizes to a second DNA molecule having a nucleotide sequence as shown in SEQ ID NO: 2 or 4.

In yet another embodiment of the present invention a method of producing an interferon-gamma-inducible mammalian protein is provided which comprises the steps of:

providing a host cell comprising an intron-free DNA molecule encoding a mammalian MIG, said DNA molecule hybridizing to a second DNA molecule having a nucleotide sequence as shown in SEQ ID NO: 2 or 4;

culturing the host cell in a nutrient medium so that the interferon-gamma-inducible mammalian protein is secreted into the medium; and harvesting the interferon-gamma-inducible mammalian protein from the nutrient medium.

In still another embodiment of the invention a nucleotide probe is provided which hybridizes to an intron-free DNA molecule encoding a mammalian MIG, said DNA molecule hybridizing to a second DNA molecule having a nucleotide sequence as shown in SEQ ID NO: 2 or 4.

In yet another embodiment of the invention a composition is provided which comprises antibodies which are immunoreactive with a mammalian MIG having a sequence selected from those shown in SEQ ID NO: 1 and 3.

These and other embodiments of the invention which will be described in more detail below, provide the art with novel molecules involved in responses to immunological and inflammatory stimuli.

BRIEF DESCRIPTION OF THE DRAWINGS

FIG. 3 shows the cDNA sequence and inferred amino acid sequence of MIG-1 isolated from mouse cells.

FIG. 4 compares the homology of the amino acid sequence of MIG-1 and closely related members of the platelet factor 4 family (PF4).

FIG. 5 shows the partial cDNA sequence and inferred amino acid sequence of MIG-2 isolated from human cells.

FIG. 6 shows a comparison between human MIG-2 amino acid sequences predicted from cDNA sequences and corresponding mouse MIG-1 predicted amino acid sequences. Mismatches are indicated with vertical lines and lower case letters in the MIG-1 sequence.

DETAILED DESCRIPTION OF THE INVENTION

Figure 1A:
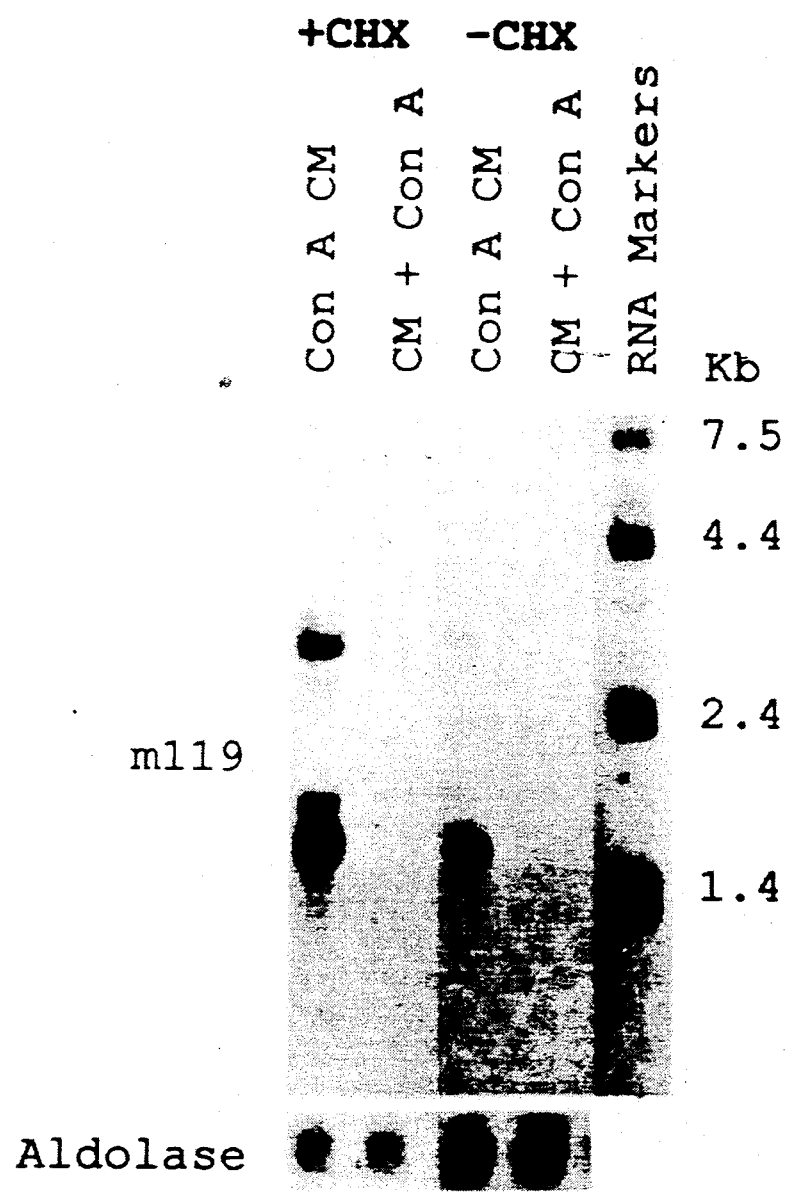
FIG. 1 shows an RNA blot analysis of MIG-1 mRNA in the RAW 264.7 cell line. Panel A: cells treated with conditioned medium from concananvalin A (Con A)-stimulated spleen cells; probes consisted of $^{32}$P-labeled mll9 (MIG-1) and aldolase A cDNAs. Panel B: cells treated with lipopolysaccharide (LPS), IFN-$\alpha$,-$\beta$- and $\gamma$, as indicated; probes as in panel A. Panel C: time course of response to IFN-$\gamma$ (100 units/ml).

It is a discovery of the present invention that novel cytokines are produced by interferon-$\gamma$-treated mammalian monocytes. These cytokines are presumed to mediate at least a subset of the functions expressed by the macrophages in response to interferon-$\gamma$. Thus it is expected that they could be used to mimic at least some of the effects of interferon-$\gamma$. Because of the wide involvement of macrophages in processes relevant to human health and disease, these cytokines are of potential therapeutic value.

Two such cytokines, called herein MIGs, for monokines induced by gamma interferon, have been identified and characterized in detail. One of these was identified in a mouse monocyte/macrophage cell line and is called MIG-1, and the second was identified in a human monocytic cell line and is called MIG-2. Both of these proteins are members of the platelet factor 4 family of cytokines, with which they share approximately 13-35% homology. MIG-1 and MIG-2 share about 70% homology with each other. These monokines do not appear to be mouse: human homologs of each other. The size of their messenger RNAs are about 1.6 kb and about 2.8 kb, respectively. In addition, when mouse genomic DNA is hybridized with probes derived from MIG-1 and MIG-2 in Southern blots, different genomic fragments are detected by the two probes. This suggests that MIG-2 shares a greater degree of homology with an unidentified mouse gene than with MIG-1.

As shown in SEQ ID NO: 1, MIG-1 comprises a sequence of 126 amino acids. It has a predicted cleavage site between a putative signal sequence and the mature form of the protein after glycine-21. Cleavage of an in vitro translation product of in vitro transcribed cDNA having the sequence shown in SEQ ID NO: 2 by canine microsomes is consistent with cleavage of the predicted signal peptide and with MIG-1 being a secreted protein. MIG-2 comprises 125 amino acids. The molecular weight of MIG-2 that has been translated in vitro in the absence of microsomes is about 14 to 18 kD as determined on SDS gels, and it too is subject to cleavage in a canine microsome system to a species having a mobility similar to a 14.3 kD marker protein.

MIG proteins, nucleotide sequences, probes and antibodies can be used to bioassay for interferon-$\gamma$. For example, to quantify the amount of interferon-$\gamma$ in a sample containing an unknown quantity of interferon-$\gamma$, a portion of the sample can be applied to a macrophage or monocytic cell line. The amount of MIG proteins, or MIG messenger RNA which is made in response to the applied interferon-$\gamma$ can be quantified. Quantification can be accomplished using any means known in the art, such as radioimmunoassay, Northern blots, Western blots, enzyme linked immunoadsorbent assay, etc. The amount of MIG protein or mRNA produced by the cells in response to the applied interferon-$\gamma$ correlates with the amount of interferon-$\gamma$ in the sample.

MIG proteins can also be used to mimic a subset of the activities of interferon-$\gamma$. Although the set of therapeutic uses of the interferons continues to be expanded, against both cancers (Volberding, 1985 Semin. Oncol. vol. 12, (4 suppl) pp. 2–6) and infectious diseases (Jacyna, 1990. Br. Med. Bull. vol 46, pp. 368–382), their therapeutic usefulness has been limited by their toxicities (Sarna, 1987, "Interferons and interleukin-2 as therapy for malignancy and the acquired immunodeficiency syndrome", pp. 260–263, in Fahey, J. L. moderator. Immune interventions in disease. Ann. Intern. Med. 106:257-274.) The use of the MIGs may accomplish the therapeutic benefits of interferon-$\gamma$ without the associated toxicities.

The mammalian MIGs of the present invention may be derived from a variety of species sources. Human and mouse MIGs are described in detail herein, but other animal sources are also suitable. For instance, bovine, ovine, porcine, and rat genomes are all expected to contain MIG genes. Mammalian MIGs include proteins that share significant homology with MIG-1 and MIG-2. This includes proteins having at least about 70% amino acid identity and preferably those having at least about 90% amino acid identity with MIG-1 or MIG-2. Other MIG proteins may be isolated from humans and mice which are closely related to MIG-1 and MIG-2. Mammalian MIG proteins may be inducible by interferon-$\gamma$.

Other MIG genes can be isolated, either by the method by which the murine MIG sequence was isolated, or by the method by which the human MIG sequence was isolated. These methods are described in more detail below. Briefly, the murine MIG sequence was isolated using differential hybridization. Two probes were prepared: (1) cDNA prepared from a macrophage cell line stimulated with a lymphokine-rich conditioned medium from mitogen-stimulated mouse spleen cells; and (2) cDNA prepared from control cells of the macrophage cell line which were not treated with the lymphokine-rich conditioned medium. A population of cDNA was derived from mRNA isolated from stimulated macrophage cells; the MIG cDNA isolated from this population of cDNA was selected on the basis of its preferential hybridization to the first probe. Interferon-γ can be used in place of the lymphokine-rich conditioned medium. The human MIG cDNA sequence was isolated from stimulated human monocytes and screened using murine MIG cDNA sequences as a probe. This is described in more detail below.

An intron-free DNA molecule, according to the present invention, may comprise cDNA which has been transcribed via reverse transcriptase from mRNA isolated from mammalian cells. Alternatively, the intron-free DNA molecule may have been derived from mRNA as described above, but may be propagated as cloned cDNA in other cells. The intron-free DNA may thus be covalently linked to other sequences, such as plasmids or phages, to facilitate replication.

The intron-free DNA molecules of the present invention which encode mammalian MIGs hybridize to reference DNA molecules which are defined by their sequences. See SEQ ID NO: 2 and 4. Various conditions for carrying out hybridizations are known in the art. Manipulation of the conditions is also known so that sequences of differing degrees of homology will hybridize. Low stringency conditions are known which allow molecules having somewhat divergent sequences to hybridize. High stringency conditions are also known which require high levels of homology to achieve hybridization. High stringency conditions, according to the present invention are such that sequences diverging by more than 10% do not hybridize. Such conditions are useful to detect sequences which are closely related. Lower stringency conditions may allow detection of sequences which differ by as much as about 30%. The sequences which are important for comparing homology are the coding sequences. Non-coding regions may differ more than these stated amounts without changing the relationship of the sequences as members of the MIG family.

The MIG proteins of the invention are substantially free of other mammalian proteins. This generally means that preparations of protein are contemplated in which at least 95% and preferably 98% of the mammalian protein comprises MIG. This level of purity can be readily achieved by expressing the mammalian MIG protein in a non-mammalian cell, such as a prokaryote. Under such conditions, even non-purified MIG will be substantially free of other mammalian protein. Alternatively, if the MIG is expressed in a mammalian cell or tissue, purification can be readily accomplished using immunological techniques, such as immunoaffinity chromatography, or immunoprecipitation, employing antibodies immunoreactive with mammalian MIG. Such antibodies are described in more detail below. Standard protein purification techniques can also be employed to purify MIG proteins.

Host cells according to the present invention carry an intron-free DNA molecule which encodes a mammalian MIG protein or a portion of a MIG protein. The host cells may be transformed, transfected, fused, electroporated, or otherwise modified to introduce the intron-free DNA molecule of the present invention. Choice of a suitable host cell is easily within the skill of the art. Prokaryotic cells such as $E.$ $coli$ are often used to replicate DNA molecules and express heterologous proteins. According to one aspect of the present invention a fusion protein is produced which is a hybrid molecule comprising a portion of a bacteriophage protein and all or a portion of a mammalian MIG. Methods for making gene fusions and expressing fusion proteins are well known in the art.

According to another aspect of the present invention the intron-free DNA molecules of the present invention are replicated and expressed in eukaryotic cells. These cells are capable of processing the primary translation product of the MIG mRNA to form mature MIG protein. Typically this involves the cleavage of a signal sequence and concomitant translocation across the cell membrane into the extracellular milieu. Thus in eukaryotic cells, depending on the extent of the MIG sequences present, MIG which is expressed may be secreted into the nutrient medium. Often such eukaryotic cells will also glycosylate proteins which are expressed. The pattern of glycosylation may or may not be identical to the pattern obtained when the mammalian MIG is isolated from its natural source.

Nucleotide probes for the detection of MIG sequences are also contemplated. These can be used to isolate additional MIGs from other species sources, as described above for the isolation of human MIG using murine MIG as a probe. Alternatively, the probes can be used to quantitate mRNA which is specific for MIG. Nucleotide probes are generally at least 14 nucleotides in length, which correspond in sequence to one of the MIG nucleotide sequences disclosed in the subject application. Typically the probes are labeled using radioactive or biotin-linked groups which allow detection of hybrids formed comprising the probes.

Antibodies which are immunoreactive with mammalian MIG proteins are also contemplated by the present invention. Such antibodies may bind to both MIG-1 and MIG-2 or may be specific, binding to only one of the MIG proteins. The antibodies may be polyclonal or monoclonal. Techniques for producing antibodies which are specific for a particular protein are well known in the art. The antibodies may be isolated from animals which have been immunized with a whole MIG protein, a mixture of MIG proteins, a portion of a MIG protein, such as a synthetic polypeptide, or a fusion protein comprising all or a part of a MIG protein.

Receptors for MIG proteins can be isolated using, for example, immunoaffinity techniques. Thus mammalian cell homogenates can be subjected to immunoaffinity chromotography and proteins which bind to the column are candidates for MIG receptors. The receptors, in soluble form, can be used to inhibit the action of MIG by competition with the natural cellular targets of MIG.

The following examples are provided to illustrate various embodiments of the invention.

EXAMPLES

EXAMPLE 1

This example describes the isolation of a cDNA clone encoding MIG-1.

RAW 264.7 cells (Raschke, et al. (1978), Cell 15:261–267) were obtained from the American Type Culture Collection and grown in RPMI-1640 supplemented with 10% fetal bovine serum. Lymphokine-rich conditioned medium (CM) was prepared using concanavalin A (Con A)-stimulated spleen cells from male C57BL/6 mice according to the procedure of Marcucci et al. ((1982), Eur. J. Immunol. 12:787–790).

Poly(A)+ RNA was prepared from RAW 264.7 cells that had been exposed for 3 hours, in the presence of cycloheximide (CHX) at 10 μg/ml, to 20% CM from Con A-stimulated spleen cells. cDNA was synthesized (Gubler, et al. (1983), Gene 25:263–269) and a library was constructed in λgt10 (Huynh, et al. (1985) in *DNA Cloning Techniques, A Practical Approach*, ed. D. Glover (IRL, Oxford), Vol. 1, pp. 49–78). The library was screened by differential plaque hybridization (Lau et al. (1987), Proc. Natl. Acad. Sci. USA 84:1182–1186) using a cDNA probe prepared from RAW cells stimulated as described immediately above and using a cDNA probe prepared from control RAW cells treated for 3 hr with identical concentrations of Con A and CHX but without spleen cell CM.

cDNA clones were isolated that identified 11 mRNA species that accumulated in the RAW 264.7 cells following exposure to the spleen cell CM. As shown in FIG. 1A, one cDNA clone, 1.2 kilobases (kb) long and designated m119, hybridized to a major mRNA species of approximately 1.6 kb that was induced in RAW cells by the CM from Con A-stimulated spleen cells but not detectable in control RAW cells even with long exposure of the autoradiograph. CHX did not inhibit expression of the m119 mRNA suggesting that new protein synthesis was not required for induction. In addition to the 1.6-kb band, the m119 probe identified prominent inducible species of approximately 3.2 and 1.8 kb. The 1.8-kb band was seen only in RNA from cells stimulated in the presence of CHX. Preliminary evidence from analyses of multiple m119 cDNA clones and m119 genomic clones suggests that the 1.8-kb species is an alternatively spliced m119 mRNA. The 3.2-kb species is presumably a precursor of the 1.6-kb mRNA but has not been characterized. The level of aldolase A mRNA, shown as a control, was unaffected by exposure of RAW cells to CM from Con A-stimulated spleen cells.

EXAMPLE 2

This example demonstrates the induction of m119 mRNA by macrophage-activating factors.

To identify the lymphokines in the spleen cell CM that may have been responsible for inducing the m119 mRNA, as well as to determine which other macrophage-activating factors were capable of enhancing expression of the m119 gene, total RNA was prepared from RAW cells treated with a variety of agents for 3 and 6 hr and the RNA was analyzed by Northern blot.

Figure 1B:
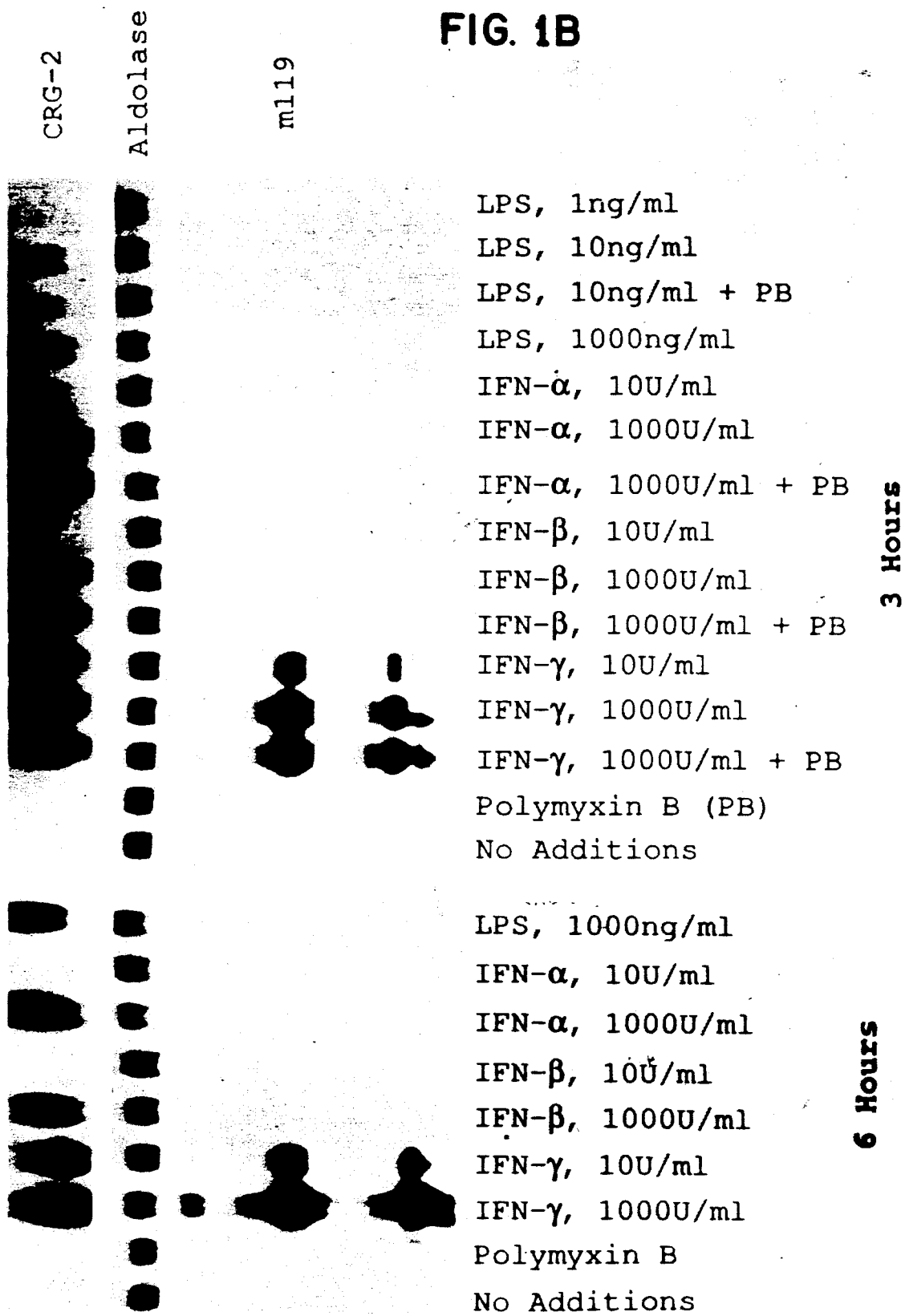

Significant induction of the m119 mRNA was seen only with IFN-$\gamma$. The results of the experiments with IFN-$\alpha$, IFN-$\beta$, IFN-$\gamma$ and LPS are shown in FIG. 1B. IFN-$\gamma$ was mouse recombinant protein with a specific activity $\geq 10^7$ units/mg (Amgen Biologicals) or $1.2 \times 10^7$ units/mg (generously provided by Genentech). The IFN-$\alpha$ and IFN-$\beta$ were murine natural products with specific activities of $1.4 \times 10^6$ international reference units (IRU)/mg and $1.3 \times 10^8$ IRU/mg, respectively (Lee BioMolecular Laboratories, San Diego, Calif.). All other cytokines were obtained from Genzyme, Boston, Mass. When cycloheximide (CHX) was used, it was added simultaneously with the activator at 10 μg/ml. When assayed for endotoxin, medium saved following treatment of the RAW 264.7 cells with each of the cytokines gave levels of <0.5 endotoxin unit/ml (chromogenic Limulus amoebocyte lysate test, Whittaker Bioproducts). LPS used to activate cells was from *Escherichia coli* 0127:B8 (Difco).

The selective induction of the m119 mRNA in RAW 264.7 cells by IFN-$\gamma$ was reproducible and was not due to an inability of RAW cells to respond to IFN-$\alpha$, IFN-$\beta$, or LPS. For example, shown in FIG. 1B is the induction by all the IFNs and LPS of crg-2, another of the genes that had been identified as responsive to the Con A-stimulated spleen cell CM. In addition to the results with IFN-$\alpha$, IFN-$\beta$, and LPS, treatment of RAW cells with recombinant murine IL-1$\alpha$, recombinant murine IL-3, recombinant murine IL-4, recombinant murine granulocyte/macrophage colony-stimulating factor, recombinant human colony-stimulating factor 1, poly-(I)-poly(C), the calcium ionophore A23187, phorbol 12-myristate 13-acetate, and the combination of A23187 and phorbol myristate acetate all failed to induce the m119 mRNA, nor was the m119 mRNA induced by serum (i.e., mitogen) stimulation of serum-starved BALB/c 3T3 fibroblasts (data not shown).

Figure 1C:
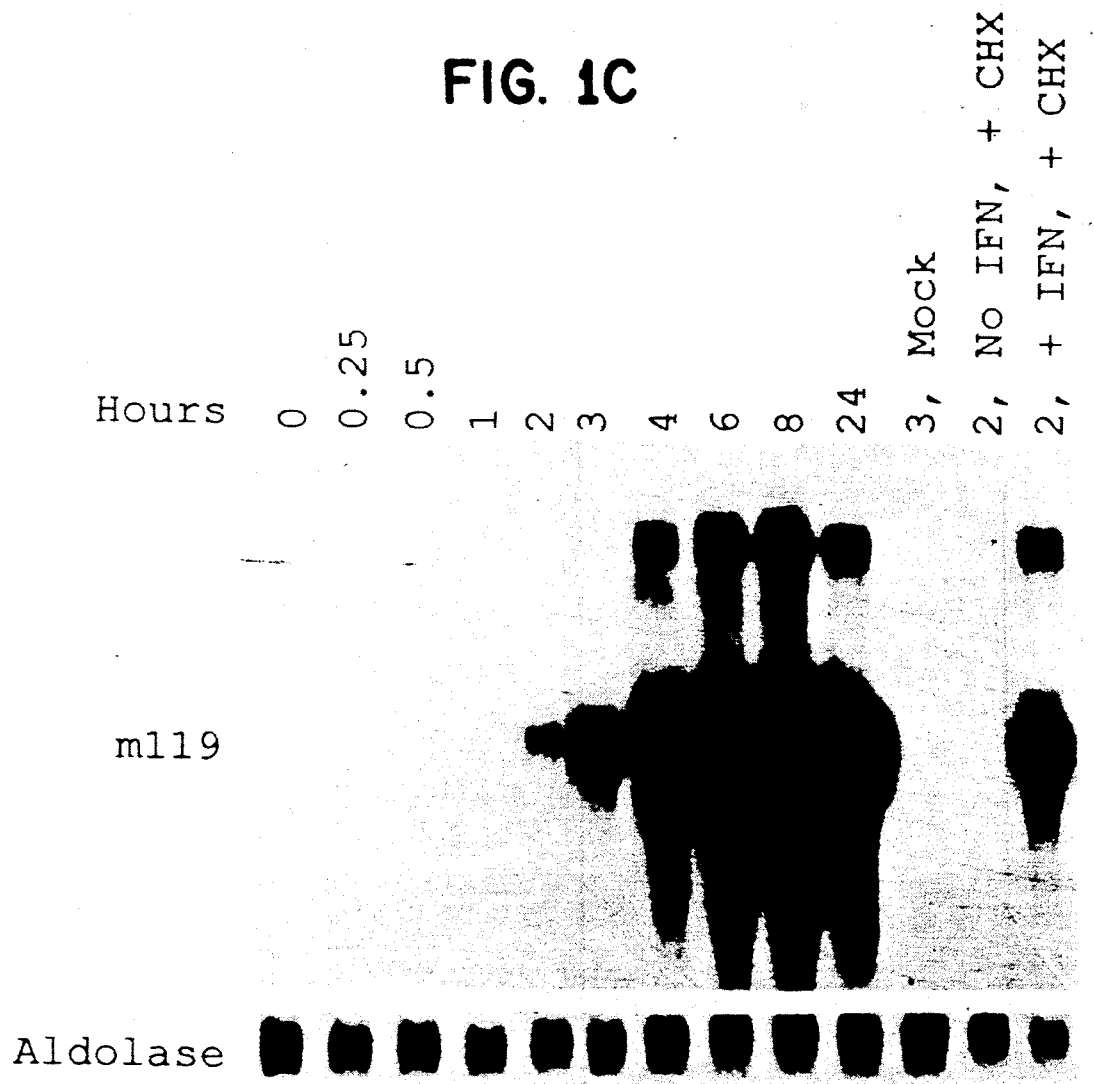

To determine the time course of induction of the m119 mRNA in response to IFN-$\gamma$, RNA was prepared from RAW cells treated for 0–24 hr. The m119 mRNA was induced rapidly and dramatically, as shown in FIG. 1C, reaching a maximum between 6 and 24 hr. As in the case of treatment with the spleen cell CM, induction by IFN-$\gamma$ did not appear to require new protein synthesis. In fact, the addition of CHX led to superinduction of the m119 mRNA.

While IFN-$\gamma$ led to an immediate and marked stimulation of m119 gene expression, what is particularly striking is the degree of specificity of induction of the m119 gene by IFN-$\gamma$, exceptional even among those genes previously reported to be induced by IFN-$\gamma$ preferentially (Luster, et al., supra; Fan, et al. supra,) which suggests a unique relationship between IFN-$\gamma$ and m119, both in terms of IFN-$\gamma$ regulated gene expression and as regards the biological actions of IFN-$\gamma$.

EXAMPLE 3

This example shows the induction of MIG-1 mRNA in normal macrophages.

Figure 2:
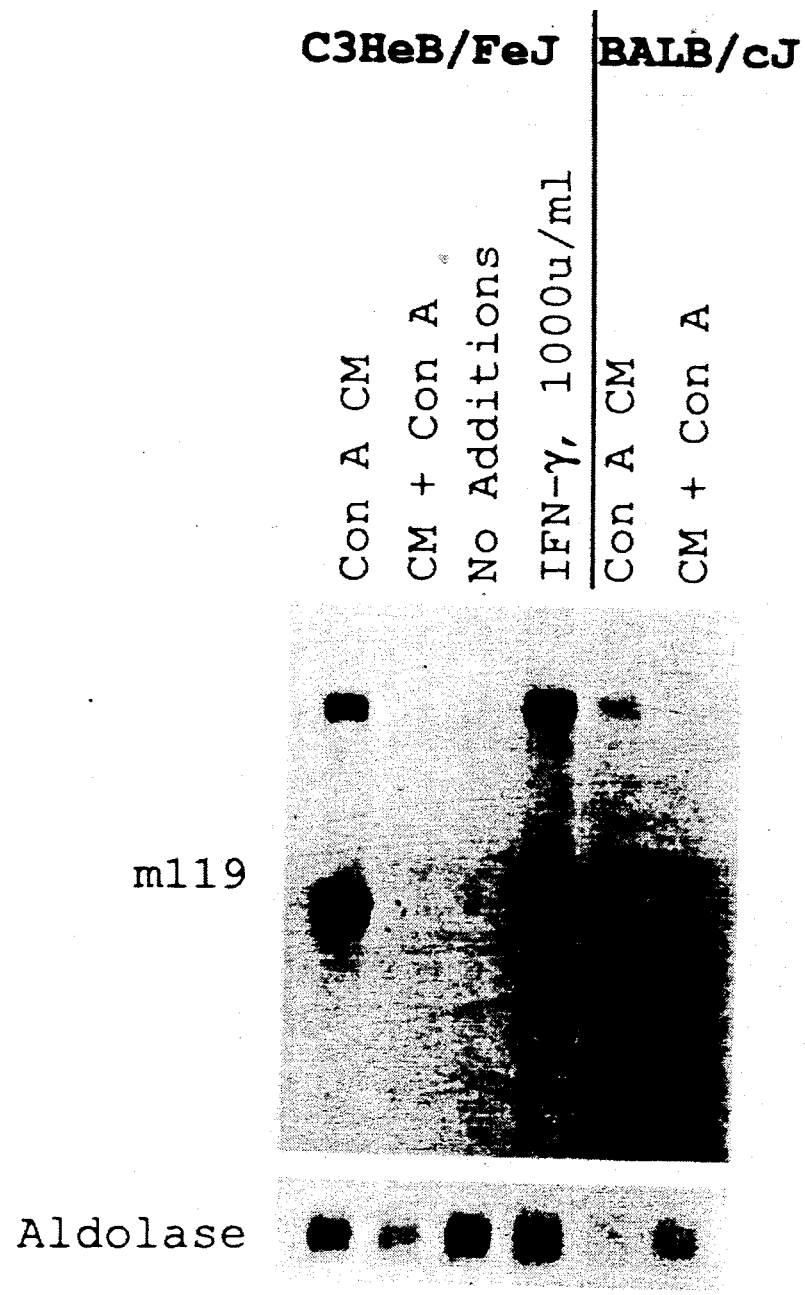
FIG. 2 demonstrates the expression of MIG-1 mRNA in peritoneal exudate cells in response to stimuli as indicated.

To demonstrate the induction of m119 mRNA during the activation of normal macrophages, m119 gene expression was analyzed in the adherent population from starch-elicited peritoneal exudate cells obtained from both C3HeB/FeJ and BALB/cJ mice. As shown in FIG. 2, when these cells (>80% macrophages as determined by morphology) were exposed to CM from Con A-stimulated spleen cells, m119 mRNA was induced. Exposure of the C3HeB/FeJ cells to IFN-$\gamma$ likewise led to the expression of the m119 gene. The electrophoretic mobilities of the m119 mRNA species from peritoneal cells as compared to RAW cells were identical.

EXAMPLE 4

This example shows the sequences of the MIG-1 cDNA and the MIG-1 predicted protein.

Overlapping deletions for sequencing of cDNA clones inserted into the Bluescript phagemid (Stratagene) were made using exonuclease III, buffers, S$_1$ nuclease, and T$_4$ DNA ligase (Promega) according to the vendor's protocols. DNA sequencing was done by the dideoxy chain-termination method (Sanger, et al. (1977) Proc. Natl. Acad. Sci. USA 74:5463-5467) with reagents from United States Biochemical.

Portions of the original 1.2-kb m119 cDNA clones were used as probes to isolate a nearly full-length 1.4-kb cDNA, whose sequence is shown in FIG. 3. Primer extension using RNA from IFN-γ-stimulated RAW cells identified 5' termini of m119 mRNA species at five adjacent positions (data not shown), and the predominant start site for transcription is designated by the arrow in FIG. 3. m119 genomic clones were isolated from a BALB/c mouse library (Clontech Laboratories), and a 1.7-kb EcoRI fragment was used to obtain genomic sequence that overlapped the 5' end of the m119 cDNA, providing the sequence of mRNA missing from the cDNA clone. As shown in FIG. 3, the genomic sequence contains an A+T-rich region (TAAATAAATAT) at positions −32 to −22 that includes several possible "TATA boxes." The m119 mRNA contains 1247 nucleotides exclusive of the poly(A) tail, with a single long open reading frame from the first AUG methionine codon beginning at nucleotide +58 to a termination codon UAA at nucleotides 436–438. This open reading frame encodes a predicted protein of 126 amino acids of relative molecular mass ($M_r$) 14,461. The sequence GCC that precedes the presumed initiation codon comforms to Kozak's consensus sequence ((1987) Nucleic Acids Res. 15:8125-8148). The 3' end of the cDNA does not contain the typical AATAAA polyadenylylation sequence but does contain, 22 nucleotides 5' of the poly(A) tail, the sequence AGTAAA, which has been reported to serve as a signal for polyadenylylation (Ucker (1983) Mol. Cell. Biol. 3:551-561).

The N-terminal sequence of the predicted m119 protein has the characteristics of a signal peptide of a secreted or transmembrane protein, and the −3, −1 rule of von Heijne ((1986) Nucleic Acids Res. 14:4683-4690) predicts signal-peptide cleavage after Gly-21. m119 is unlikely to be a transmembrane protein because it lacks a second long hydrophobic sequence. There is a single predicted site for N-linked glycosylation at Asn-58. Of additional note is an extremely basic C-terminal sequence.

EXAMPLE 4

This example demonstrates the relationship of MIG-1 to other members of the PF4 family.

Comparisons of the m119 protein sequence to those in the National Biomedical Research Foundation library (June, 1990) indicated that MIG-1 is a new member of a family of proteins with ancestral relationships to PF4, a platelet granule protein (Deuel et al. (1981) Proc. Natl. Acad. Sci. USA 78:4584-4587). A comparison of the homology of the m119 predicted amino acid sequence with the sequences of the most closely related members of the family is shown in FIG. 4. The percent identity of amino acids within the cysteine window (Cys Window) is shown. The Cys Window is defined as the highly homologous region between and including the first and fourth cysteines of the four cysteines found invariantly among members of the platelet factor 4 family. See, Oquendo, et al., *J. Biol. Chem.*, vol. 264, pp. 4133-37, 1989; Vanguri and Farber, *J. Biol. Chem.*, vol. 265, pp. 15049-57, 1990; and Farber, *Proceedings of the National Academy of Sciences USA*, vol. 87, pp. 5238-43, 1990. The Cys Window occurs at residues 31-74 (inclusive) in MIG-2 and residues 30-73 (inclusive) in MIG-1. The sequence comparisons suggest that although related to these other members of the family, MIG-1 is neither identical to, nor the mouse homologue of any of those members previously described.

The members of the PF4 family are low molecular weight factors secreted by cells including fibroblasts, macrophages, and endothelial cells in response to a variety of stimuli such as growth factors, interferons, viral transformation, and bacterial products. Biological activities for some members of the family have been identified and include autocrine growth stimulation of a human melanoma line by Gro/MGSA (Richmond et al., (1988) EMBO J. 7:2025-2033), regulation of neutrophil-endothelial cell adhesion by IL-8 (Gimbrone, et al. (1989), Science 246:1601-1603), angiostatic activity by PF4 (Maione et al. (1990), Science 247:77-79), and chemotactic activity by PF4 (Deuel, et al. (1981) Proc. Natl. Acad. Sci. USA 78:4584-4587), IL-8 (Matsushima, et al. (1988), J. Exp. Med. 167:1883-1893), MIP-2 (Wolpe, et al. (1989) Proc. Natl. Acad. Sci. USA 86:612-616), and β-thromboglobulin (Senior, et al. (1983), J. Cell. Biol. 96:382-385). These cytokines are likely to be involved in the control of immune and inflammatory responses, tissue injury, growth and repair. The selective responsiveness of the MIG-1 gene in macrophages to IFN-γ suggests that the MIG-1 protein may have a role in those effects on macrophages specific to IFN-γ, such as the priming of macrophages for the release of reactive oxygen intermediates (Nathan, et al. (1984), J. Exp. Med. 160:600-605). If MIG-1 is selectively induced by IFN-γ in cells other than macrophages, the MIG-1 protein would be a candidate to mediate additional IFN-γ-specific activities such as the induction of the major histocompatibility complex class II antigen (Rosa, et al. (1983), EMBO J. 2:1585-1589).

EXAMPLE 5

This example demonstrates the isolation of MIG-2 cDNA from human cells.

The human monocytic cell line THP-1 was obtained from the American Type Culture Collection and was grown in RPMI 1640 with 10% fetal bovine serum (Innovar) and 50 μM β-mercaptoethanol. Nine×$10^7$ THP-1 cells were stimulated for 8 h with 1000 U/ml recombinant human gamma-interferon (Collaborative Research) and 27 μg poly (A)+ RNA was prepared using the FastTrack RNA isolation kit (Invitrogen). Five μg of poly(A)+ RNA was used to prepare a cDNA library in the Uni-ZAP ™ XR vector (Stratagene) according to the protocol and with reagents supplied by Stratagene, except that first strand cDNA synthesis was performed using SuperScript ™ reverse transcriptase (BRL) and buffer supplied by BRL. The library was amplified on *E. coli* host strain PLK-F' (Stratagene). The library was plated on PLK-F' cells and screened with a probe prepared by nick translation from a full length 119/MIG cDNA (cDNA 119/24). The probe had a specific activity of 1×$10^9$ cpm/μg and was used at 1.6×$10^6$ cpm/ml. Hybridization was done in 1M NaCl, 50 mM Na phosphate pH 6.5, 2 mM EDTA, 0.5% SDS, 10 X Denhardt's at 65° for 20 h, followed by the following washes at 65°, in succession: 1M NaCl, 50 mM TRIS-HCl pH 8.6, 2 mM EDTA, 1% SDS, 1 h×2; 0.5M NaCl, 25 mM Na phosphate pH 6.5, 0.5% SDS×1; 0.5M NaCl, 25 mM Na phosphate pH 8.5, 2 mM EDTA, 0.5% SDS×1 h. A final rinse was done in 2×SSC at room temperature.

Hybridizing plaques were picked and subsequent platings and hybridizations done for plaque purification. Plasmid rescue was done from positive recombinant phage using the R408 helper phage with reagents and according to the protocol supplied by Stratagene. Plasmid DNA was prepared by the alkaline lysis/SDS method and purification on a CsCl gradient. The largest cDNA clone, H-1-3, was 2.5 kb. Sequencing the ends of the cDNA clone was done by the dideoxy chain termination method using T3 and T7 primers supplied by Stratagene and using reagents and protocols supplied by United States Biomedical. Sequences of cDNAs H-1-3, H-5-2c, H-2-2, and H-4-2 demonstrated that they were independent overlapping cDNA clones. The sequence presented in FIG. 5 is a composite of sequences from cDNA clones H-1-3 and H-5-2c and the majority of the sequence represents the results in each case from a single strand. The initiator methionine is assigned based on alignment with the mouse MIG-1 sequence.

EXAMPLE 6

The predicted amino acid sequences of murine MIG-1 and human MIG-2 are aligned and compared in FIG. 6. Eighty-eight amino acids are identical out of the 125 amino acids of MIG-2 or the 126 amino acids of MIG-1. The identities were scored with two gaps introduced as shown in the figure.

EXAMPLE 7

This example shows the induction of MIG-2 mRNA in human monocytic cells by recombinant human interferon-γ and that the induction of MIG-2 mRNA is inhibited to a large extent by cycloheximide (CHX), a protein synthesis inhibitor.

Figure 7:
FIG. 7 shows a Northern blot of human RNA probed with MIG-2 sequences. The presence or absence of interferon-$\gamma$ (IFN-$\gamma$) and cycloheximide (CHX) in the medium prior to harvesting of RNA is indicated above each line.

THP-1 and U937, human monocytic cells, were treated with interferon-γ (1000 U/ml) for 8 hours. Cycloheximide, when used, was added at 50 μg/ml 15 minutes before the addition of interferon-γ. RNA was extracted from the treated cells and hybridized to MIG-2 cDNA in Northern blots. As shown in FIG. 7, a message of 2.8 kb was detected in human cells, which was induced by IFN-γ. The induction was dramatically inhibited by cycloheximide, suggesting the need for new protein synthesis to effect induction of MIG-2. In contrast, MIG-1 induction in mouse cells appears insensitive to cycloheximide.

EXAMPLE 8

This example shows that MIG-1 and MIG-2 probes do not hybridize to the same mouse genomic fragments.

Forty-four μg of mouse genomic DNA digested with EcoR I, EcoR V, Sac I and Bgl I were divided in two and run on a single 0.7% agarose gel. After transfer, the filter was cut in two. Hybridizations with MIG-1 and MIG-2 cDNA probes were in hybridization buffer containing 1M NaCl at 65° C. for one day and at 60° C. for two days, and washes at 0.5M NaCl at 60° C. M (marker) lanes contain a DNA ladder where a subset of the fragments hybridized to the probes. The sizes of the EcoR I fragments of the 119/MIG-1 gene and of one of the ladder fragments are indicated.

Figure 8:
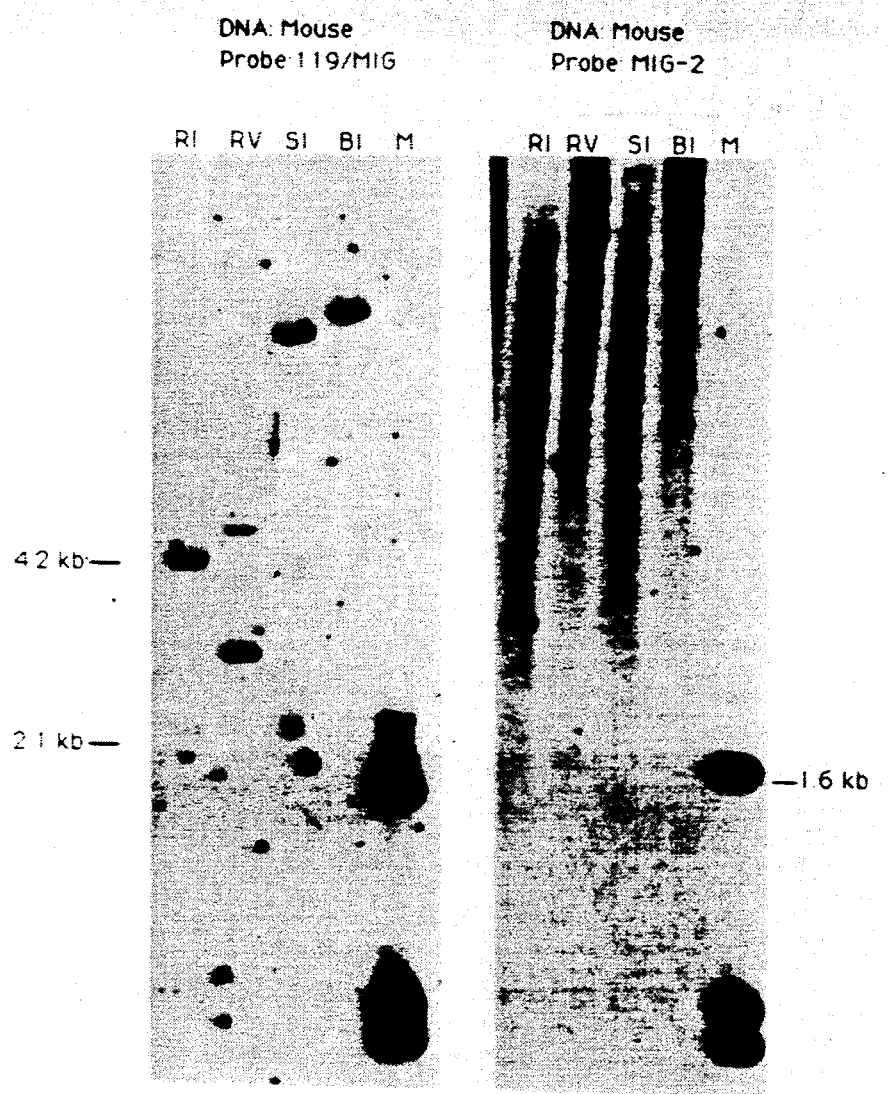
FIG. 8 shows a Southern blot of mouse genomic DNA probed with MIG-1 and MIG-2 cDNA probes. Lanes designations are: RI (EcoRI), RV(EcoRV), SI(-SacI), BI(BgII), M(markers).

As can be seen in FIG. 8, the MIG-2 probe hybridized to at least one genomic fragment in mouse DNA that did not correspond to the MIG-1 gene. In addition, MIG-2 did not hybridize to any fragments representing the MIG-1 gene. The results suggests that MIG-1 and MIG-2 are not true homologues. The Southern blot predicts the existence of at least one additional MIG-2 related gene in the mouse. Just as recent evidence points to a group of gro/MIP-2—related genes in the PF4 family (Tekamp-Olson et al., J. Exp. Med. 172:911–919 (1990)), so too there may be a group of 119/MIG-1 related genes. MIG-2 is, in any case, a newly identified, gamma IFN-induced human member of the PF4 family.

EXAMPLE 9

This example suggests that both MIG-1 and MIG-2 are secreted proteins.

RNA was transcribed from the MIG-1 and MIG-2 cDNA clones in vitro and used for in vitro translation without and with added microsomal membranes. Sense and anti-sense RNA was transcribed and capped in vitro from cDNAs in the Bluescript phagemid using reagents and protocols supplied by Stratagene. One half μg of RNA was used in a 25 μl translation reaction with or without canine pancreatic microsomal membranes using reagents and protocols supplied by Promega. The MIG-2 reaction contained [$^{35}$S]-cysteine and the other reactions [$^{35}$S]-methionine. In each case except for MIG-2, 1.25 μl of the reaction was run per lane and for MIG-2, 0.8 μl was used. Samples were reduced and analyzed on a 12% gel. The smear in the MIG-2 lanes between 6.2 and 14.3 kDa is related to the use of [$^{35}$S]-cysteine.

Figure 9:
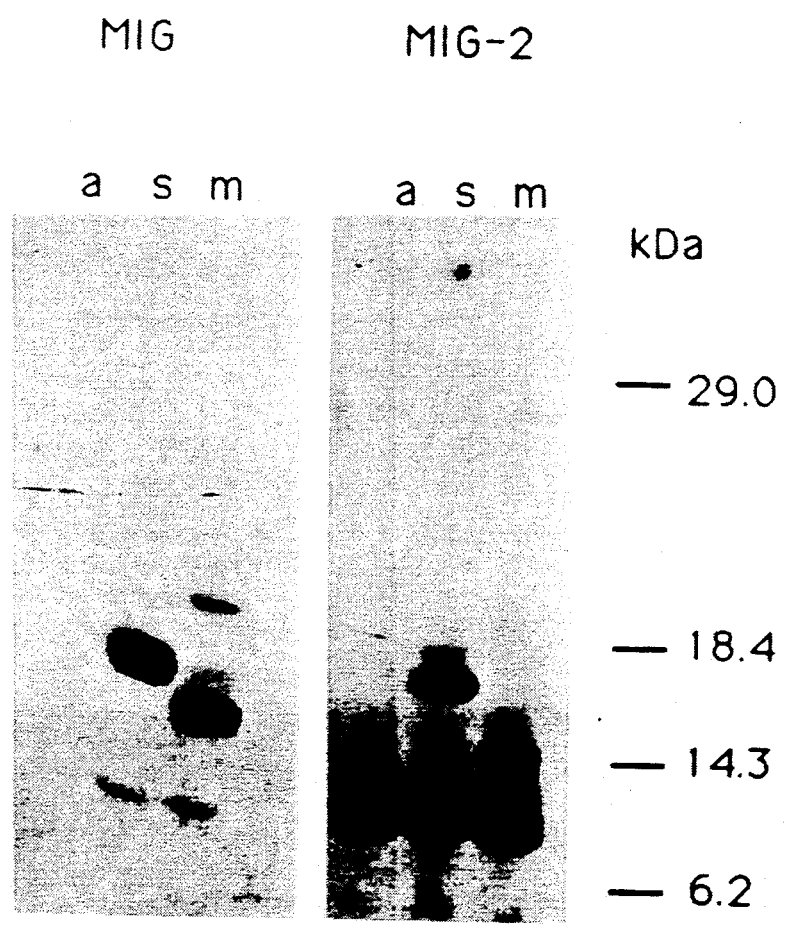
FIG. 9 shows the results of in vitro transcription/translation of MIG-1 and MIG-2 cDNAs. The result of translations in the presence of canine microsomes is also shown. Lane designations are a: antisense RNA; s: sense RNA; and m: sense RNA and microsomes.

FIG. 9 demonstrates that in each case, the microsomal membranes increased the mobility of the translation product, indicating recognition and cleavage of the signal peptides, consistent with these proteins being secreted. Of note is that in the case of MIG-1 the translation with microsomes give rise reproducibly to a faint lower mobility band of >18.4 kDa, suggesting that MIG-1 may be glycosylated, consistent with its predicted sequences. Mobility of the MIG-1 polypeptide is slower than anticipated from the MIG-1 predicted amino acid sequence, a phenomena observed for other PF4 family members (Richmond et al., (1988) EMBO J. vol 7, pp. 2025-33; and Leonard, et al. (1990) Immunol. Today, vol 11, pp. 97–101).

EXAMPLE 10

This example demonstrates the expression of MIG-1 and MIG-2 antigens and the raising of anti-MIG antiserum.

Figure 10:
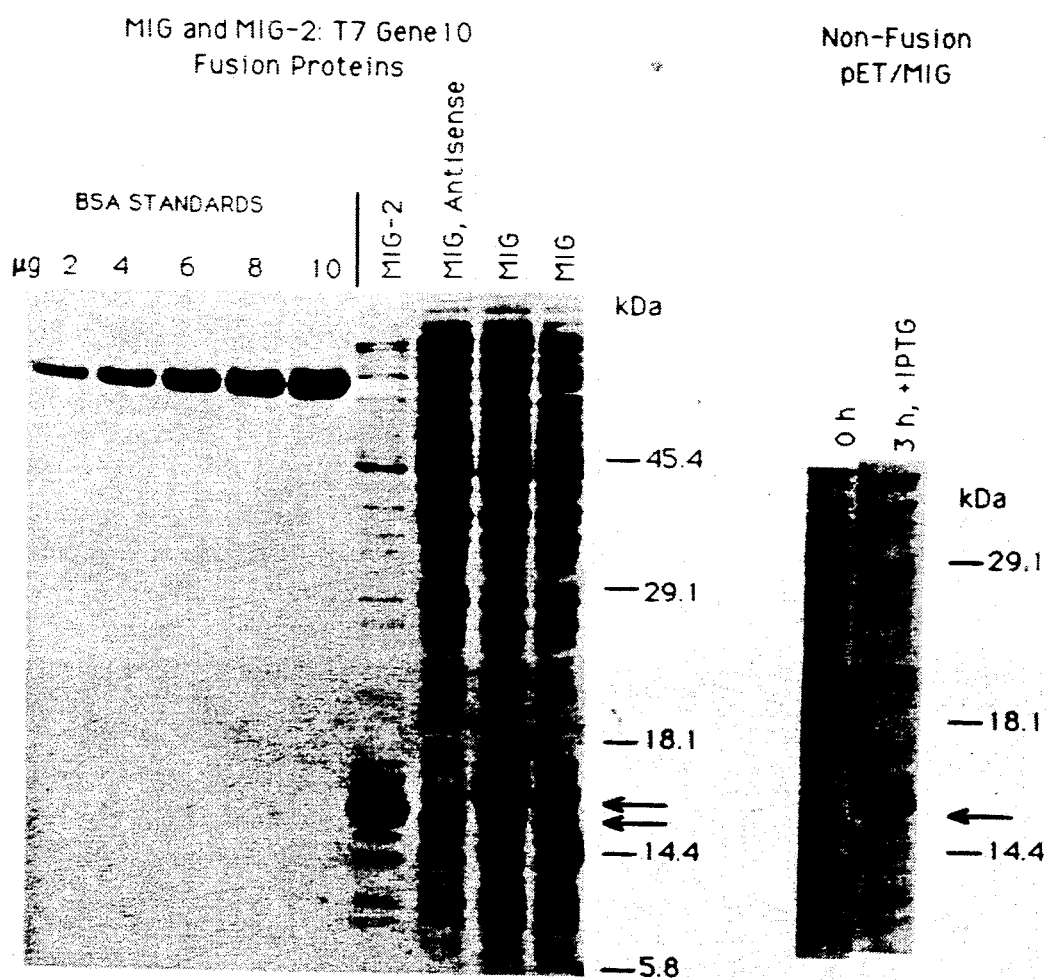
FIG. 10 shows the production of MIG-related proteins in E. coli which are useful as antigens to obtain MIG-specific antiserum.

MIG-1 and MIG-2 cDNAs minus the sequences encoding the predicted signal peptides were inserted in the pET-3b vector (Studier et al. Meth. Enz. 185:60–89, (1990)) with 13 amino acids of the T7 gene 10 protein fused to the MIG-1 and MIG-2 sequences. Cultures of *E. coli* containing these plasmids were induced for 3 h with IPTG and extracts of 150 μl of cultures analyzed by reducing SDS-PAGE (FIG. 10). Two different cultures producing MIG-1 fusion proteins were analyzed and are shown in panel A. Cells containing a pET-3b plasmid with MIG-1 sequences inserted in the reverse orientation were included as a control. The upper arrow indicates the MIG-1 fusion protein, and the lower arrow the MIG-2 fusion protein, each present in separate lanes. Non-fusion MIG-1 protein, lacking signal peptide, was expressed from a pET-8c-MIG plasmid and is shown in panel B. Lanes contain lysates of 100 μl of bacterial cultures that were treated as indicated and analyzed by staining with Coomassie Blue. An arrow indicates MIG-1 protein. The fusion proteins have been prepared in quantity and injected into rabbits to raise anti-sera. The non-fusion protein may be useful as an immunoaffinity reagent to purify antibody and might also have biological activity.

---

I claim:

1. An intron-free DNA molecule encoding a mammalian MIG protein which has the nucleotide sequence shown in SEQ ID NO: 2 or 4.

2. The intron-free DNA molecule of claim 1 which encodes a protein having the amino acid sequence shown in SEQ ID NO: 1 or 3.

3. The intron-free DNA molecule of claim 1 which is derived from a mouse.

4. The intron-free DNA molecule of claim 2 which is derived from a mouse.

5. The intron-free DNA molecule of claim 1 which is derived from a human.

6. The intron-free DNA molecule of claim 2 which is derived from a human.

7. A host cell which comprises a DNA molecule of claim 1 which has the nucleotide sequence shown in SEQ ID NO: 2 or 4.

8. A host cell which comprises a DNA molecule of claim 2 which encodes a protein having the amino acid sequence shown in SEQ ID NO: 1 or 3.

9. A method of producing a mammalian MIG protein, comprising the steps of:
providing a host cell comprising the DNA molecule of claim 1;
culturing the host cell in a nutrient medium so that the mammalian MIG protein is secreted into the medium; and
harvesting the mammalian MIG protein from the nutrient medium.

10. The method of claim 9 in which the DNA molecule encodes a protein having the amino acid sequence shown in SEQ ID NO: 1 or 3.

11. The method of claim 9 wherein the host cell comprises an intron-free DNA molecule which has the nucleotide sequence shown in SEQ ID NO: 2 or 4.

12. The method of claim 9 wherein the host cell comprises an intron-free DNA molecule which encodes a protein having the amino acid sequence shown in SEQ ID NO: 1 or 3.

* * * * *